United States Patent
Walker et al.

(10) Patent No.: US 7,699,776 B2
(45) Date of Patent: Apr. 20, 2010

(54) INTUITIVE ULTRASONIC IMAGING SYSTEM AND RELATED METHOD THEREOF

(75) Inventors: William F. Walker, Charlottesville, VA (US); John A. Hossack, Charlottesville, VA (US); Travis N. Blalock, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1322 days.

(21) Appl. No.: 10/506,722

(22) PCT Filed: Mar. 6, 2003

(86) PCT No.: PCT/US03/06607

§ 371 (c)(1),
(2), (4) Date: Sep. 7, 2004

(87) PCT Pub. No.: WO03/075769

PCT Pub. Date: Sep. 18, 2003

(65) Prior Publication Data

US 2005/0154303 A1    Jul. 14, 2005

Related U.S. Application Data

(60) Provisional application No. 60/362,763, filed on Mar. 8, 2002.

(51) Int. Cl.
*A61B 8/00* (2006.01)
(52) U.S. Cl. ...................... 600/437; 600/443
(58) Field of Classification Search ......... 600/437–445, 600/455, 443, 459, 453, 447, 450, 463, 446, 600/468; 601/1–4; 607/28, 301
See application file for complete search history.

(56) References Cited

U.S. PATENT DOCUMENTS

| 4,596,256 | A | * | 6/1986 | Ascher et al. | 600/523 |
|---|---|---|---|---|---|
| 4,730,495 | A | * | 3/1988 | Green | 73/620 |
| 5,014,712 | A | * | 5/1991 | O'Donnell | 600/447 |
| 5,549,708 | A | * | 8/1996 | Thorne et al. | 604/110 |
| 5,617,864 | A | | 4/1997 | Stouffer et al. | |
| 5,961,465 | A | | 10/1999 | Kelly, Jr. et al. | |
| 6,132,379 | A | | 10/2000 | Patacsil et al. | |
| 6,139,496 | A | | 10/2000 | Chen et al. | |
| 6,245,017 | B1 | * | 6/2001 | Hashimoto et al. | 600/447 |
| 6,251,073 | B1 | | 6/2001 | Imran et al. | |
| 6,325,759 | B1 | * | 12/2001 | Pelissier | 600/443 |

(Continued)

FOREIGN PATENT DOCUMENTS

EP    0763344 A2    3/1997

(Continued)

*Primary Examiner*—Eric F Winakur
*Assistant Examiner*—Lawrence N Laryea
(74) *Attorney, Agent, or Firm*—McDonnell Boehnen Hulbert & Berghoff LLP

(57) ABSTRACT

A hand held ultrasonic instrument (10) is provided in a portable unit that performs C-Mode imaging and collects 3D image data. In a preferred embodiment a transducer array (60), display unit (20), beamformer (40), power system, and image processor are integrated in one enclosure weighing less than three pounds. In operation, the portable unit is scanned across a target and the displayed image is conveniently presented to the operator whereby the displayed image corresponds exactly to the target, or a scaled fashion if desired.

49 Claims, 7 Drawing Sheets

U.S. PATENT DOCUMENTS 6,488,625 B1 * 12/2002 Randall et al. .............. 600/437
6,544,177 B1 * 4/2003 Robinson .................... 600/443
6,962,566 B2 * 11/2005 Quistgaard et al. .......... 600/437
7,141,020 B2 * 11/2006 Poland et al. ............... 600/447

FOREIGN PATENT DOCUMENTS

EP 0815793 A2 1/1998
EP 0875203 A2 11/1998

* cited by examiner

INTUITIVE ULTRASONIC IMAGING SYSTEM AND RELATED METHOD THEREOF

CROSS-REFERENCES TO RELATED APPLICATIONS

This application is a national stage filing of International Application No. PCT/US03/06607, filed on Mar. 6, 2003, which claims benefit under 35 U.S.C Section 119(e) from U.S. Provisional Application Ser. No. 60/362,763, filed Mar. 8, 2002, entitled "An Intuitive Ultrasonic Imaging System and Related Method thereof," the entire disclosures of which are hereby incorporated by reference herein in their entirety.

FIELD OF THE INVENTION

The present invention is directed to ultrasonic diagnostic systems and methods and, in particular, a substantially integrated hand held ultrasonic diagnostic instrument.

BACKGROUND OF THE INVENTION

Medical imaging is a field dominated by high cost systems that are so complex as to require specialized technicians for operation and the services of experienced medical doctors and nurses for image interpretation. Medical ultrasound, which is considered a low cost modality, utilizes imaging systems costing as much as $250K. These systems are operated by technicians with two years of training or specialized physicians. This high-tech, high-cost approach works very well for critical diagnostic procedures. However it makes ultrasound impractical for many of the routine tasks for which it would be clinically useful.

A number of companies have attempted to develop low cost, easy to use systems for more routine use. The most notable effort is that by Sonosite. Their system produces very high quality images at a system cost of approximately $20,000. While far less expensive than high-end systems, these systems are still very sophisticated and require a well-trained operator. Furthermore, at this price few new applications are opened.

The applicability of conventional ultrasound is further limited by the typical image format used. Images are produced in what is commonly referred to as a B-Mode format, representing a tomographic slice through the body perpendicular to the skin surface. This image format is non-intuitive and the simple act or process of mentally registering the B-Mode image to the patients anatomy requires significant experience.

Most existing ultrasonic imaging systems utilize an array transducer that is connected to beamformer circuitry through a cable, and a display that is usually connected directly to or integrated with the beamformer. This approach is attractive because it allows the beamformer electronics to be as large as is needed to produce an economical system. In addition, the display may be of a very high quality. Unfortunately this configuration is not intuitive for most users because the image appears far from the patient. Furthermore, these systems typically acquire B-mode images, that is, images consisting of a tomographic slice taken perpendicular to the face of the transducer array. Most new users find images in this format very difficult to interpret and to register mentally with the tissue geometry. Conventional system configurations can be awkward to use because of the lengthy cable involved. Finally, the typical large size of the beamformer limits the system's portability.

Some conventional system architectures have been improved upon through reductions in beamformer size. One of the most notable efforts has been undertaken by Advanced Technologies Laboratories and then continued by a spin-off company, Sonosite. U.S. Pat. No. 6,135,961 to Pflugrath et al., entitled "Ultrasonic Signal Processor for a Hand Held Ultrasonic Diagnostic Instrument," hereby incorporated by reference herein in its entirety, describes some of the signal processing employed to produce a highly portable ultrasonic imaging system. The Pflugrath '961 patent makes reference to an earlier patent, U.S. Pat. No. 5,817,024 to Ogle et al., entitled, "Hand Held Ultrasonic Diagnostic Instrument with Digital Beamformer," hereby incorporated by reference herein in its entirety. While the titles of these patents refer to a hand-held ultrasound system, neither integrates the display and transducer unit. In U.S. Pat. No. 6,203,498 to Bunce et al., entitled "Ultrasonic Imaging Device with Integral Display," hereby incorporated by reference herein in its entirety, however, the transducer, beamformer, and display are all integrated to produce a very small and convenient imaging system. The Bunce '498 system, however, has some imitations. For example, but not limited thereto, Bunce '498 continues to use the confusing b-mode image format and its configuration is not intuitive for some users making it difficult for an untrained user to interpret the image and connect it to the organ, target, or subject under investigation.

The present invention ultrasonic imaging system and method provides the opportunity to be a common component of nearly every medical examination and procedure. The present invention provides a system and method which shall be referred to as "sonic window".

The present invention system may be produced, and the related method performed, at a low cost and will be nearly as easy to use as a magnifying glass.

The present invention ultrasonic imaging system and method provides the potential to have a broad and significant impact in healthcare. The instant document identifies various clinical applications of the present invention sonic window, but should not be limited thereto, and other applications will become attained as clinicians gain access to the system and method.

SUMMARY OF INVENTION

The present invention comprises a hand held ultrasonic instrument that is provided in a portable unit which performs C-Mode imaging and collects 3D image data. In a preferred embodiment a transducer array, display unit, beamformer, power system, and image processor are integrated in one enclosure weighing less than three pounds. In operation, the portable unit is scanned across a target and the displayed image is conveniently presented to the operator whereby the dimension of the displayed image corresponds exactly to the dimension of the target. Alternatively, the displayed image is a scaled version of the target. If scaled, then the image may be magnified or reduced accordingly.

In one aspect, the present invention provides an ultrasonic imaging system capable of producing C-Mode images and/or collecting 3D image data of a target. The system comprising: a housing; a transducer array disposed on the housing; a display unit disposed on the housing, wherein the transducer array and the display unit are integrated with the housing; and a beamformer is in communication with the system. Alternatively, the beamformer may be integrated within the housing.

In another aspect, the present invention provides a method of imaging a target to produce C-Mode ultrasonic images and/or collect ultrasonic 3D image data. The method comprising the steps of: providing a housing; providing a transducer array disposed on the housing, the transducer for transmitting ultrasonic energy into the target and receiving ultrasonic echo signals from the target; beamforming the received echo signals to provide data; processing the beamformed data; and providing a display unit disposed on the housing, the display unit displaying the processed data.

BRIEF DESCRIPTION OF THE DRAWINGS

The foregoing and other objects, features and advantages of the present invention, as ell as the invention itself, will be more fully understood from the following description of referred embodiments, when read together with the accompanying drawings in which.

DETAILED DESCRIPTION OF THE INVENTION

The present invention provides a new ultrasound system architecture and related method thereof that eliminates many of the problems and limitations associated with conventional architectures. The present invention system and method, termed the sonic window, integrates the transducer array and the display unit so that the ultrasound image is displayed at the location it is acquired. More significantly, the sonic window obtains C-Mode mages, that is, images in which the image plane is parallel to the surface of the transducer.

Novice ultrasound users, among other types of users, would find the present invention system and method very useful and beneficial. C-Mode image formats are discussed in U.S. Pat. No. 6,245,017 to Hashimoto et al., entitled "3D Ultrasonic Diagnostic Apparatus," hereby incorporated by reference herein in its entirety, as well numerous other patents. The present invention sonic window may also acquire and display 3-D images (and/or transmit the images to exterior devices for display).

The C-Mode image of the present invention and method may be selected from an arbitrary depth depending upon user preference and the specific target or tissue of interest. A preferred embodiment would include a simple user control, such as a thumbwheel, to select the depth of image acquisition. Likewise, a preferred embodiment would also include a simple display indicating the depth selected.

Figure 1A:
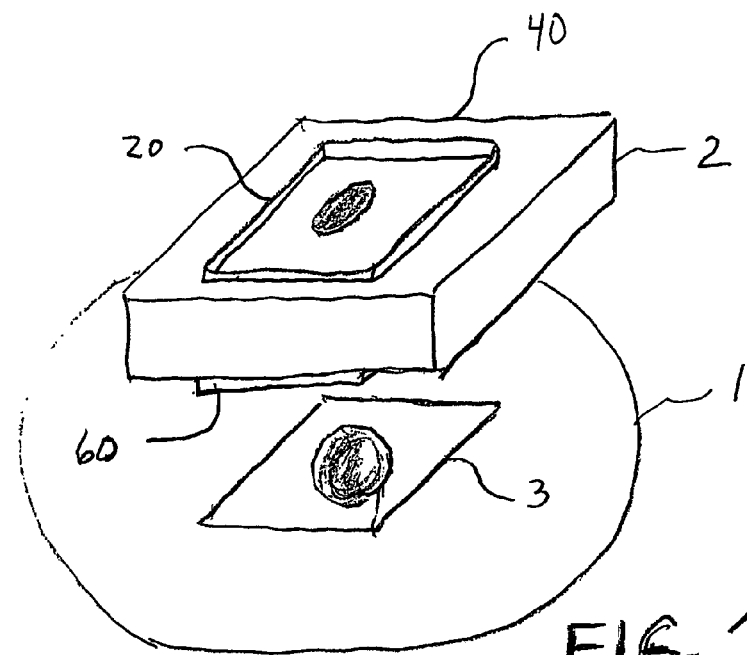
FIGS. 1A and 1B illustrate schematic representations of the present invention ultrasonic imaging system having an integrated beamformer and a stand alone beamformer, respectively.

As shown in FIG. 1A, the present invention imaging system utilizes a transducer array 60 that is in communication with beamformer circuitry 40 and a display 20 in communication to the beamformer 40. The transducer 60, beamformer circuitry 40, and display 20, are integrated whereby they are located in the same general housing (enclosure) or on same general platform or board. Images are formed by transmitting a series of acoustic pulses from the transducer array 60 and displaying the magnitude of the echoes received from these pulses. The beamformer 40 applies delays needed to steer and focus the acoustic pulses and echoes.

Figure 1B:
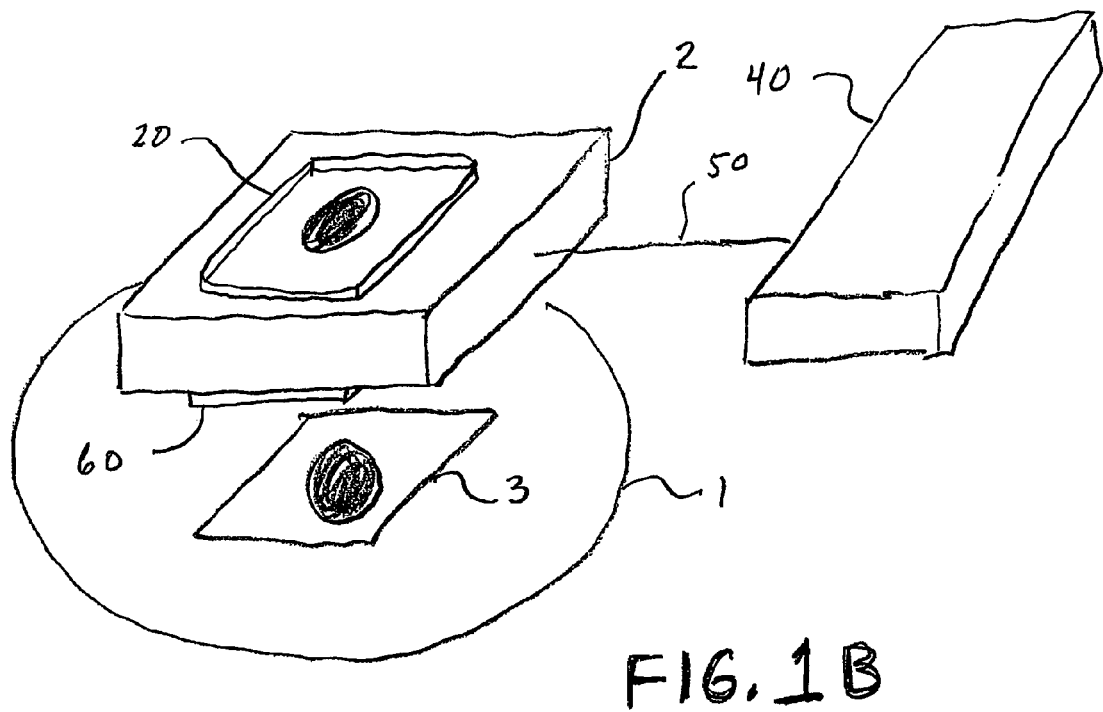

While full integration of the transducer, beamformer, and display is preferred, it should be appreciated that in some instances only the transducer and display are integrated, keeping a cable 50 to connect the transducer unit 60 and display unit 20 to a separate beamformer unit 40, as show in FIG. 1B. Rather than a cable, a channel that carries signals may be implemented using wire or cable, fiber optics, a phone line, a cellular phone link, an RF link, an infrared link, blue tooth and other communications channels.

The beamforming operations of the present invention system and method may be distributed between the transducer/display unit and a separate beamforming unit. Such a design would be intermediate between the fully integrated approach and the separate beamformer approach described above. This approach has the advantage of limiting the amount of data which must be passed between the transducer/display unit and the beamformer unit.

As the present invention system and method provides an integrated transducer unit 60 and a C-Mode or 3-D display 20, a variety of tissue information may be obtained through judicious pulse transmission and signal processing of received echoes. Such information could be displayed in conjunction with or instead of the aforementioned echo information. One such type of information is referred to as color flow Doppler as described in U.S. Pat. No. 4,573,477 to Namekawa et al., entitled "Ultrasonic Diagnostic Apparatus," hereby incorporated by reference herein in its entirety. Another useful type of information is harmonic image data as described in U.S. Pat. No. 6,251,074 to Averkiou et al., entitled "Ultrasonic Tissue Harmonic Imaging" and U.S. Pat. No. 5,632,277 to Chapman et al., entitled "Ultrasound Imaging System Employing Phase Inversion Subtraction to Enhance the Image," both of which are hereby incorporated by reference herein in their entirety. Yet another type of information that may be obtained and displayed is known as Power Doppler as described in U.S. Pat. No. 5,471,990 to Thirsk, entitled "Ultrasonic Doppler Power Measurement and Display System," hereby incorporated by reference herein in its entirety. Angular scatter information might also be displayed. Such data could be acquired using a method described in a co-pending U.S. patent application Ser. No. 10/030,958, entitled "Angular Scatter Imaging System Using Translating Apertures Algorithm and Method Thereof," filed Jun. 3, 2002, of which is hereby incorporated by reference herein in its entirety.

Speckle is a common feature of ultrasound images. While it is fundamental to the imaging process, many users find its appearance confusing and it has been shown to limit target detectability. A variety of so called compounding techniques have been described which could be valuable for reducing the appearance of speckle in sonic window images. These techniques include spatial compounding and frequency compounding, both of which are well described in the literature.

The present invention acquisition of 3-D data sets also allows a new type of compounding that might be termed "C-Mode compounding." In this technique a number of envelope detected C-Mode images from adjacent planes would be summed to yield a single speckle reduced image. While some resolution in the slice thickness dimension would be lost by this averaging, the improvement in effective signal to noise ratio achieved by reducing the speckle might outweigh that cost.

One skilled in the art would appreciate that the common practice of frequency compounding could be readily applied to the current invention. By transmitting a plurality of pulses at different frequencies and forming separate detected images using the pulses one may obtain multiple unique speckle patterns from the same target. These patterns may then be averaged to reduce the overall appearance of speckle.

The well known techniques of spatial compounding may also be applied to the current invention. The most conventional form of spatial compounding, which we call two-way or transmit-receive spatial compounding, entails the acquisition of multiple images with the active transmit and receive apertures shifted spatially between image acquisitions. This shifting operation causes the speckle patterns obtained to differ from one image to the next, enabling image averaging to reduce the speckle pattern. In another technique, which we term one-way or receive-only spatial compounding, the transmit aperture is held constant between image acquisitions while the receive aperture is shifted between image acquisitions. As with two-way spatial compounding, this technique reduces the appearance of speckle in the final image.

In many ultrasound applications the received echoes from tissue have very small amplitude, resulting in an image with poor signal to noise ratio. This problem may be addressed through the use of a technique known as coded excitation. In this method the transmitted pulse is long in time and designed so that it has a very short autocorrelation length. In this manner the pulse is transmitted and received signals are correlated with the transmitted pulse to yield a resultant signal with good signal to noise ratio, but high axial resolution (short correlation length). This method could be readily applied in the present invention sonic window device and method to improve the effective signal to noise ratio. The coded excitation technique is described in U.S. Pat. No. 5,014,712 to O'Donnell, entitled "Coded Excitation for Transmission Dynamic Focusing of Vibratory Energy Beam," hereby incorporated by reference herein in its entirety.

An aspect in fabricating a system like the present invention sonic window is in construction of the transducer array. Both cost and complexity could be reduced by incorporating a transducer fabricated using photolithographic techniques, i.e. the transducer is formed using microelectromechanical systems (MEMS). One particularly attractive approach has been described in U.S. Pat. No. 6,262,946 to Khuri-Yakub et al., entitled "Capacitive Micromachined Ultrasonic Transducer Arrays with Reduced Cross-Coupling," hereby incorporated by reference herein in its entirety.

In an embodiment, the present invention ultrasound system and method proves particularly valuable for guiding the insertion of needles and catheters. Currently, technicians attempt to insert needles based on the surface visibility of veins coupled with their knowledge of anatomy. This approach works quite well in thin, healthy individuals, but can prove extremely difficult in patients who are ill or obese. The low cost, easy to use present invention imaging system and related method provides additional guidance in these cases, increasing the efficiency of treatment, reducing patient discomfort, and improving patient outcomes by speeding treatment. Such a low cost, easy to use system would undoubtedly find additional medical applications.

Figure 3A:
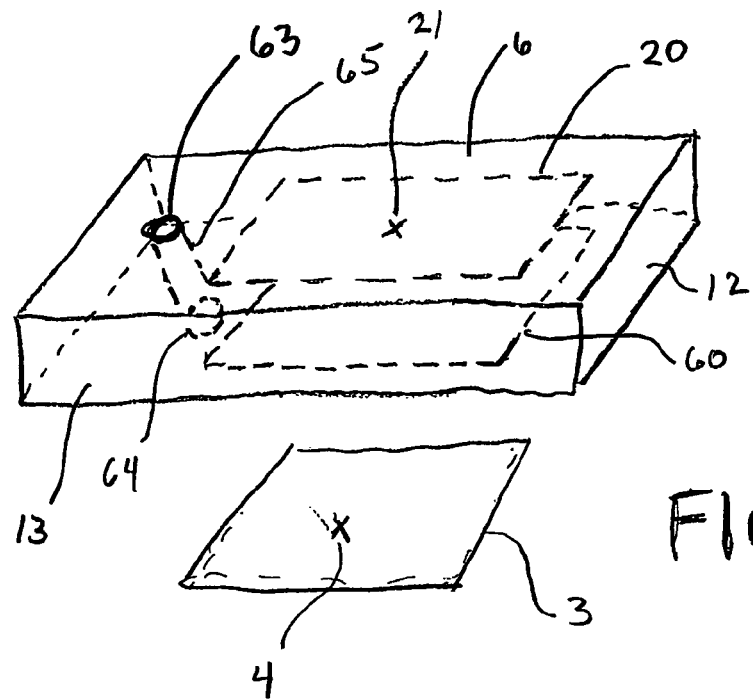
FIGS. 3A-3C schematically illustrate various embodiments of the access ports, access outlets, and passages of the hand held ultrasonic imaging system of the present invention.
Figure 3B:
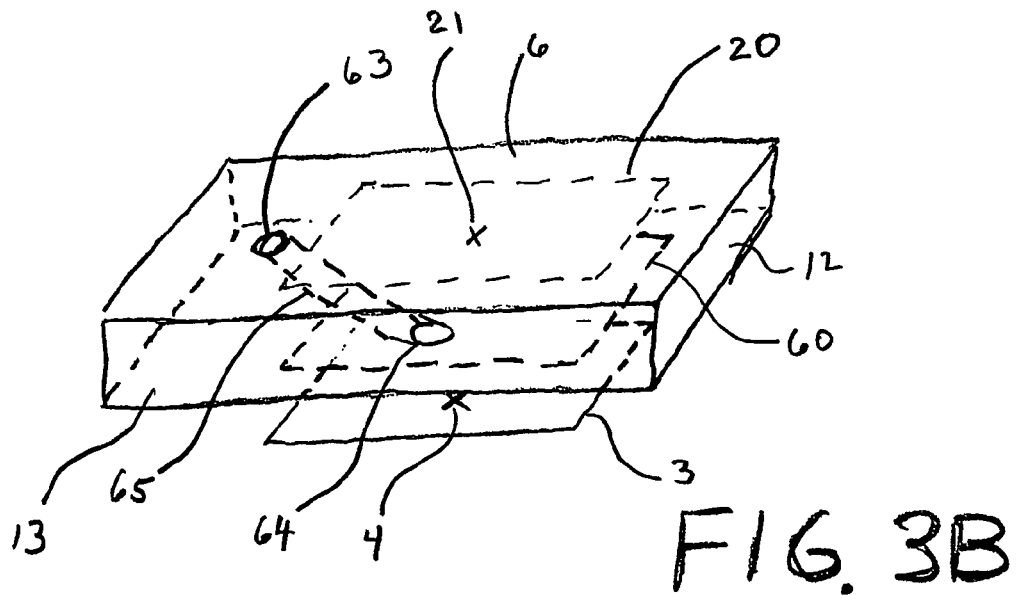
Figure 3C:
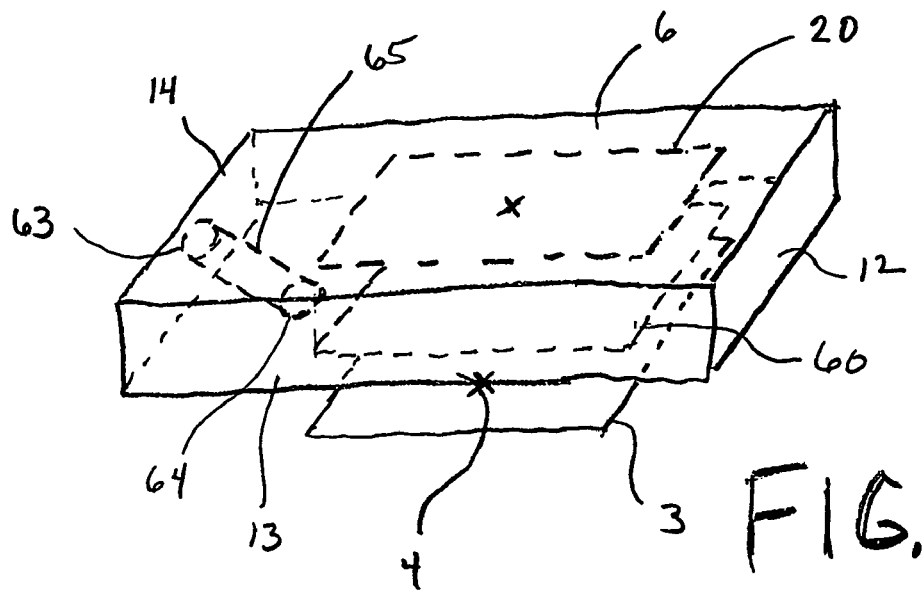

As shown in FIGS. 3A through 3C, the system 10 may have an access port 65 that is configured to receive a medical instrument, medical tool, other instruments, other tools, other needles, probes, or the like. In clinical use an instrument or needle could be inserted into the access port entry 63, pass through the device through a passage 65, and enter the tissue near the outlet 64. An instrument inserted through the passage 65 will intersect with the image plane 3 at the intersection point 4. The displayed image could readily indicate the location where an inserted needle or the like would enter the tissue or other target. The displayed image could show where the needle, instrument, and/or tool would intersect with the image, even if it doesn't actually show the needle, instrument, and/or tool. Likewise, the image could have an intersection point indicator 21 to show or indicate the location of the intersection point 4 within a given image. The location of the access port 63 is not limited to the upper surface of the device, but could also be located on any of the device sides 12, 13, 14, 15. A device may include multiple access ports 63 to enable access from different locations or simultaneous use of multiple tools. A system with multiple access ports 63 might include internal sensors (not shown) to determine which ports were in use at a given time and thereby provide appropriate indicators on the display. The outlet(s) 64 or access port entry (entries) 63 might be located within the transducer array 60 or at a location outside or adjacent to the transducer array 60, for example on the sides 12, 13, 14, 15, top 6 or bottom 8 of the housing 2, or other available components of the system 10.

It should be recognized that the access port 63, access outlet 64, and passage 65 may in combination in whole or in part include, but not limited thereto, the following: recess, aperture, port, duct, conduit, channel, pipe, tube, hose, tunnel, channel, flute, fiber optic, or equivalent structure.

For example, but not intended to be limiting, FIG. 3A schematically shows the passage 65 running from the top 6 to the bottom 8. Next, for example, but not intended to be limiting, FIG. 3B schematically shows the passage 65 running from the top 6 through transducer array 60. Still her, for example, but not intended to be limiting, FIG. 3C schematically shows the passage 65 running from one of the sides 13 (or optionally from another side 12, 14, 15) to the bottom 8 (or optionally could have been through the transducer array 60 as well).

Figure 2A:
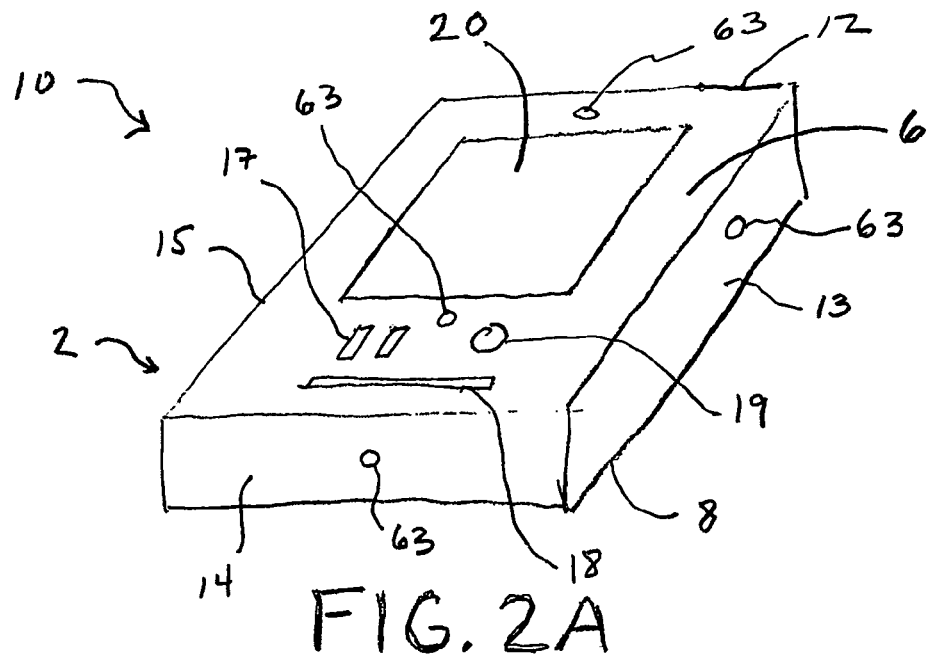
FIGS. 2A-2B schematically illustrate top and bottom perspective views, respectively, of the hand held ultrasonic imaging system of the present invention.
Figure 2B:
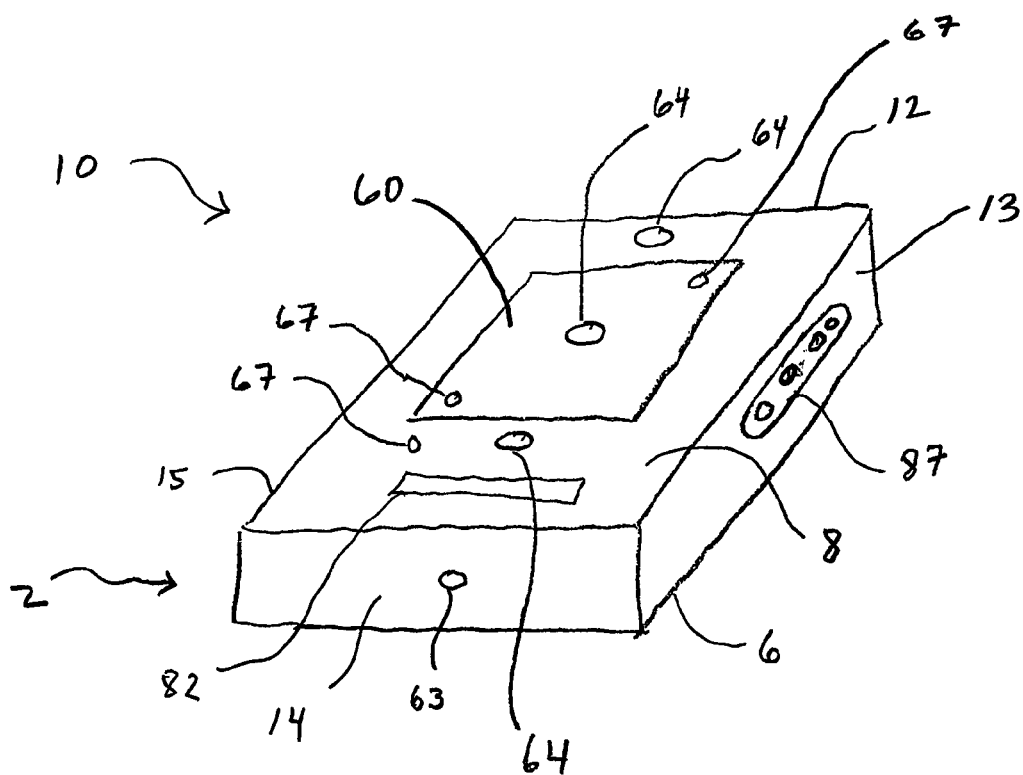

Also shown in FIG. 2B, the system may also have a transducer 60 or housing 2 incorporating a marking devices or mechanisms 67 wherein when the devices or mechanisms 67 come in contact or near contact with the target 1 (e.g., skin or surface), or when the user so instruct the system, then the marking devices or mechanisms 67 place or apply one or more marks on the target 1. Such marks may include raised bumps, indentations, dye, or other suitable means. Marks formed in this manner may be useful for guiding surgical or other interventions which will occur without the sonic window device in place. Additionally, the marks might provide useful for maintaining device registration while surgical or other medical procedures are performed with the sonic window in place. Likewise permanent or semi-permanent marks might be used to guide the sonic window to the same location during later imaging sessions. Such alignment would be facilitated by the inclusion of optical or other sensing devices (not shown) on the face of the sonic window containing the transducer array.

Still referring to FIGS. 2A-2B and 3A-3C, an embodiment of the hand held imaging system 10 is described. The system 10 comprises a housing 2 (or platform, board, enclosure, casing or the alike) preferably formed of plastic or metal or other desirable materials appreciated by those skilled in the art. The enclosure has four sides 12, 13, 14, 15 (but may be more or less according as desired), a top side 6, and a bottom side 8. The display unit 20 is on the top side 6 and transducer array 60 is on the bottom side 8, substantially or exactly parallel with the display 20. The system 10 may also have various controls for the user, for example, roller ball or toggle stick 19, alphanumeric keyboard 18, and or menu buttons 7.

Figure 7:
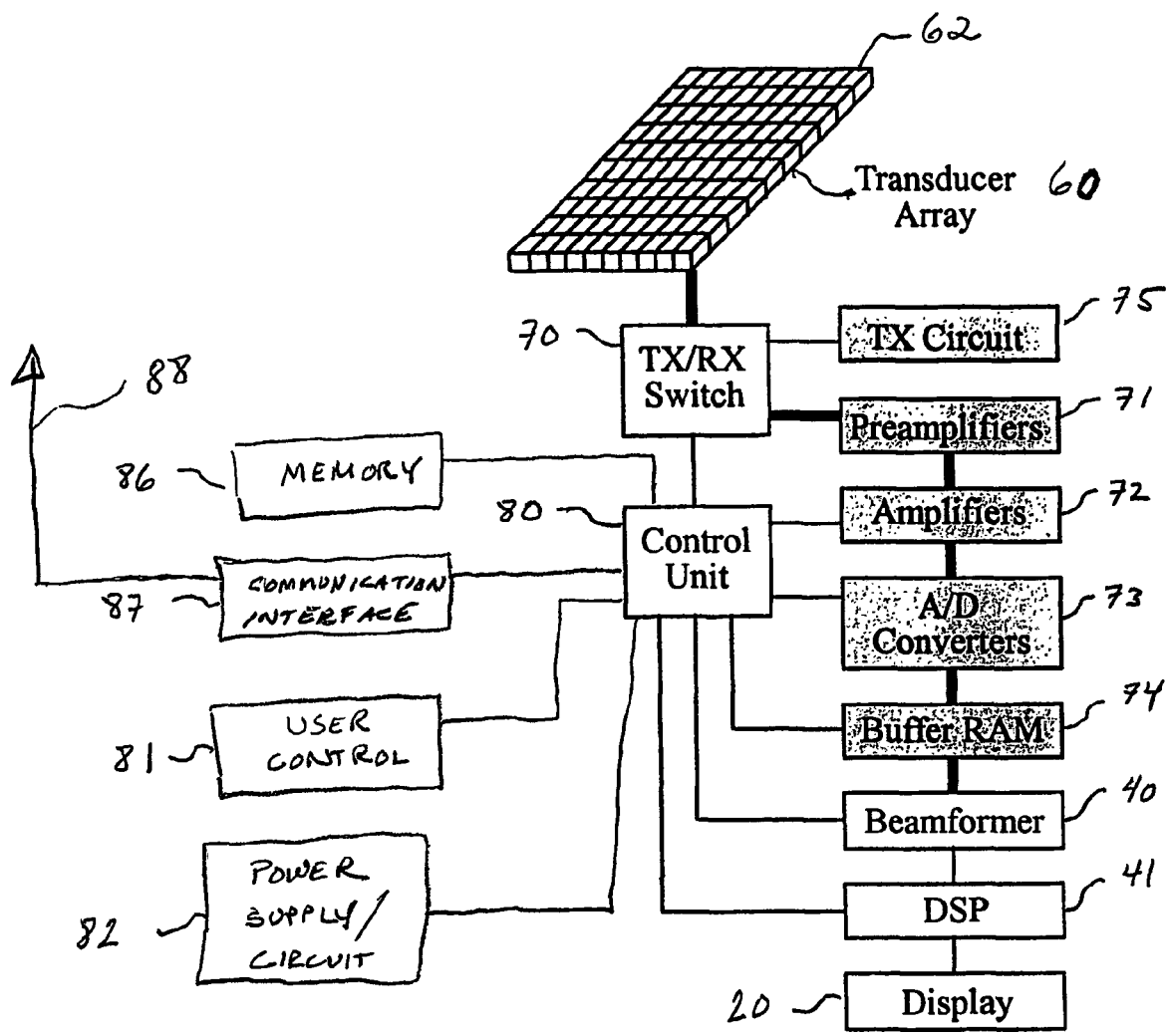
FIG. 7 illustrates in block diagram form the architecture of an embodiment of the ultrasonic imaging system of the present invention.

As best shown in FIG. 2B, the system 10 also has a communication interface 87 that is operable with a communication path or channel 88 (shown in FIG. 7). The communications interface 87, for example, allows software and data to be transferred between the system 10 and external devices. Examples of communications interface 87 may include a modem, a network interface (such as an Ethernet card), a communications port, a PCMCIA slot and card, etc. Software and data transferred via communications interface 87 are in the form of signals which may be electronic, electromagnetic, optical, or other signals capable of being received by communications interface 87. Signals are provided to communications interface 87 via a communications path (i.e., channel) 88 (as shown in FIG. 7). The Channel 88 carries signals and may be implemented using wire or cable, fiber optics, a phone line, a cellular phone link, an RF link, infrared link, blue tooth, and other communications channels. It should be noted that in general other transmission channels associated with the system may utilize similar architecture.

Figure 4:
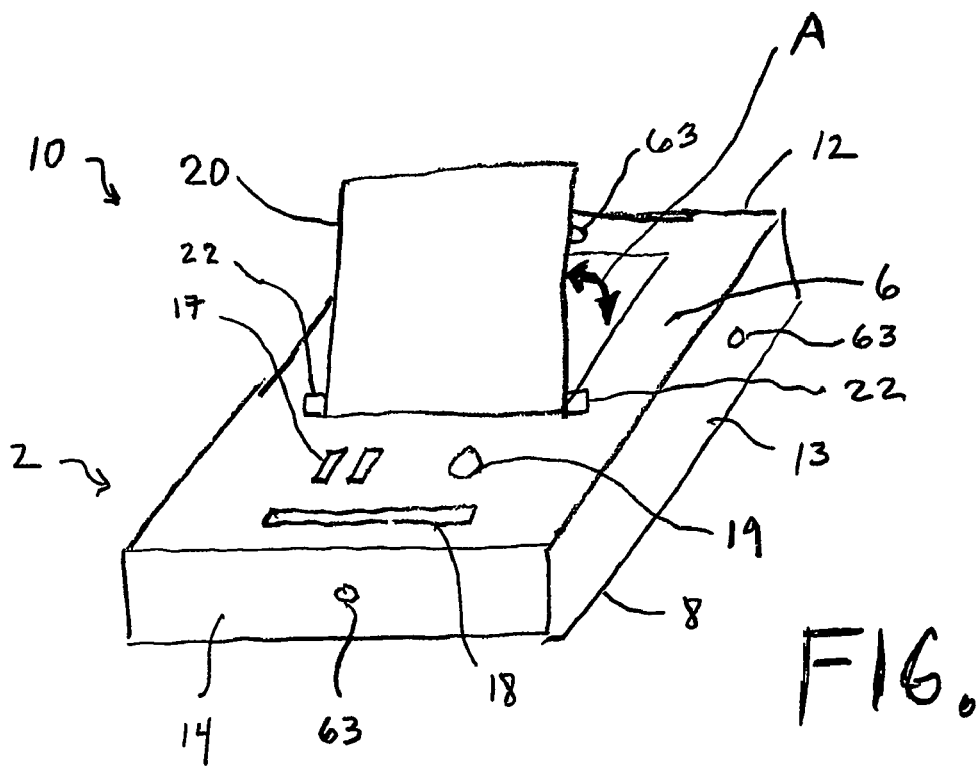
FIG. 4 schematically illustrates an adjustable display unit of the hand held ultrasonic imaging system of the present invention.

As best shown in FIG. 2A and FIG. 4, the system 10 may have a display unit 20 that may be adjustable relative to the housing 2 or other suitable structure of the system 10. In one preferred embodiment, adjustment of the angle of the display 20 would alter the angle of an image slice selected from a 3D volume of space. The user would thus be able to select the image plane of most interest by simply adjusting the display angle (e.g., from about zero to about 135 degrees), as depicted by arrow A, until that slice was displayed. This approach should provide a useful mode of navigation for novice users. FIG. 2A illustrates the display 20 in a position substantially or exactly parallel with the transducer array 60. FIG. 4 illustrates the display 20 that may be rotated in any desired angle relative to the transducer array 60. The adjustment device 22 or devices may be a variety of devices or combinations thereof including, but not limited thereto, the following: gimbal, spindle, core, axle, shaft, rod, arbor, mandrel, axis, pin, pintle, bar, journal, and bearing.

Figure 5A:
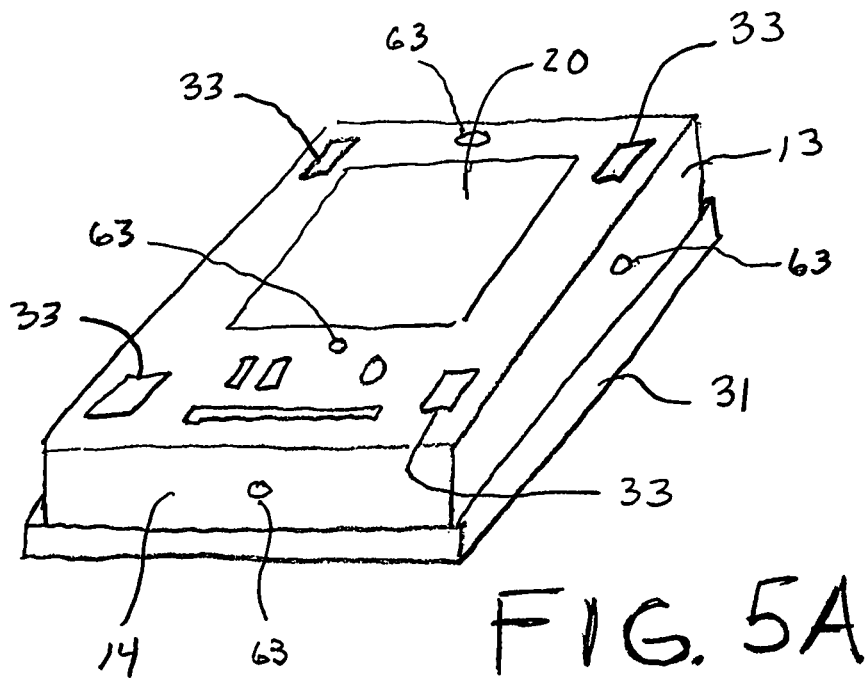
FIGS. 5A-5B schematically illustrate top and bottom perspective views, respectively, of the hand held ultrasonic imaging system of the present invention having a cover thereon, as well as adhesive devices on the housing and/or cover.
Figure 5B:
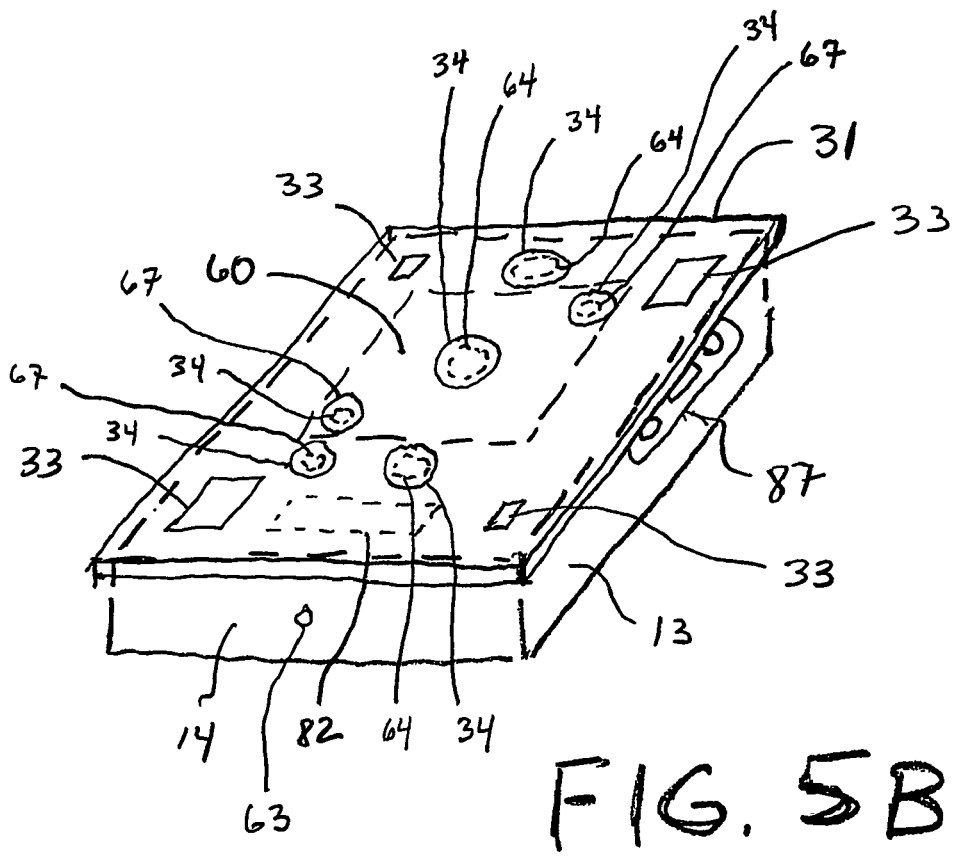

FIGS. 5A-5B schematically illustrate top and bottom perspective views, respectively, of the hand held ultrasonic imaging system of the present invention. In particular, a cover 31 or covers (removable, semi-permanent, or permanent) are provided on the bottom 8, for example, or at least a portion of the bottom 8, that is/are applied to achieve a clean, sterile, or antiseptic condition. The cover 31 would be the portion of the device in contact with the patient or target. Optionally, the cover 31 could be disposed on other areas of the housing 2 or system 10. In addition, the cover 31 may require intakes 34 or via for objects to pass through the cover 31 to the marking mechanisms 67 and/or access outlets 64. It could include portions meant to extend through the passages 65 to the access ports 63. The intakes 34 may include, but is not limited thereto, the following: perforated holes, seams, covers, plugs, lids, punch outs, doors, windows, slits, gaskets, diaphragms, valves, or other intake/access mechanisms.

The cover 31 could serve as personal protection glove. The cover 31 may be a variety of materials such as plastics, polymers, rubber, latex, metal, or any desired material. The cover 31 may include, but not limited thereto, the following: sheath, casing, well, case, shell, envelope, sleeve, or glove. Moreover, besides protecting the target or patient, the cover 31 may be used to protect the rest of the device from damage or dirt from the target or environment.

Still referring to FIGS. 5A-5B, there is schematically illustrated an adhesive device 33 or adhesive devices that may be disposed, for example on the top 6 (shown in FIG. 5A) or alternatively on the cover 33 (shown in FIG. 5B) or both to hold the system 10 in place during treatment and pre or post treatment. Optionally, the adhesive device 33 could be disposed on other areas of the housing 2 or system 10. The adhesive device 33 may include, but not limited thereto, the following: glue, adhesive, VELCRO, tape, micro-machined spikes, catch, latch or other holding mechanisms. In addition the adhesive device 33 may be incorporated entirely within the cover 31 to form an integrated cover/adhesive device.

Figure 6:
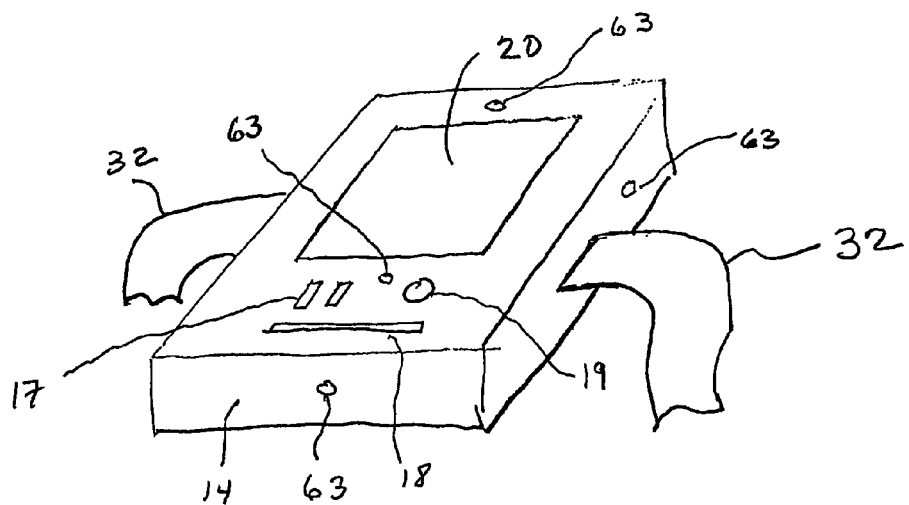
FIG. 6 schematically illustrates a top perspective view of the hand held ultrasonic imaging system of the present invention having a retaining device thereon.

Next, turning to FIG. 6, FIG. 6 schematically illustrates a top perspective view of the hand held ultrasonic imaging system of the present invention having a retaining device 32 or retaining devices that may disposed, for example on side 13 and/or side 15 (or optionally could be disposed on other areas of the housing 2 or system 10). The retaining device 32 may include, but not limited thereto, the following: strap, belt, latch, clamp, coupling, joint, keeper, connection, VELCRO, tape, or other retaining mechanisms or structures.

An advantage of the present invention ultrasonic imaging system is that it may be compact and light weight. For example, the hand held imaging system shown in FIGS. 2A-2B, 3A-3C, 4, 5A-5B, and 6, can have a variety of sizes. In one instance it may have a housing 2 with the dimensions (height, length and width) in inches of about 1×2×2, respectively. In another instance, the dimensions (height, length and width) in inches may be about 2×6×4, respectively. Of course one should appreciate that the housing size may be larger or smaller. Moreover, the hand held system 10 may be lightweight weighing less than about 2 pounds. Of course one should appreciate that it may be heavier or lighter.

Figure 8A:
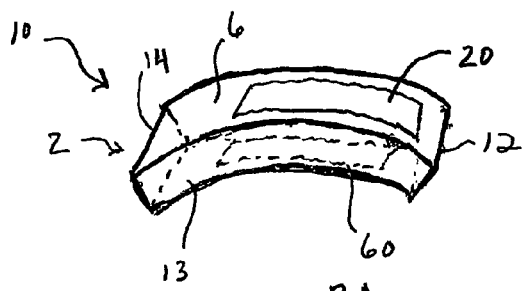
FIGS. 8A-8B, show a schematic longitudinal perspective view and lateral side view, respectively, of the hand held ultrasonic system wherein the curve of the display, housing, and/or transducer is in the longitudinal direction.
Figure 8B:
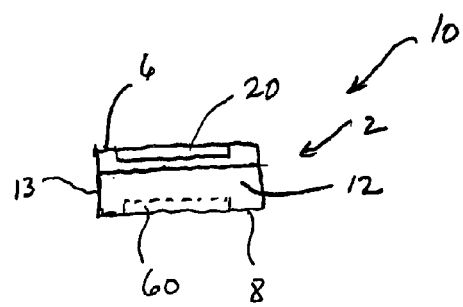
Figure 9A:
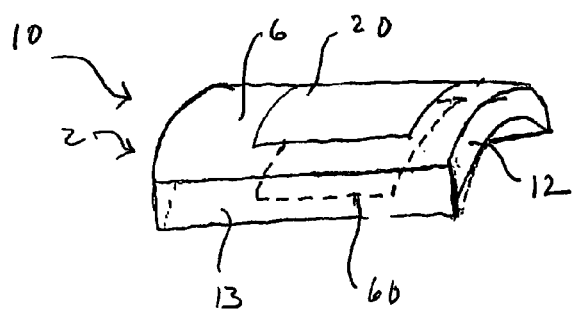
FIGS. 9A-9B, show a schematic longitudinal perspective view and lateral side view, respectively, of the hand held ultrasonic system wherein the curve of the display, housing, and/or transducer is in the lateral direction.
Figure 9B:
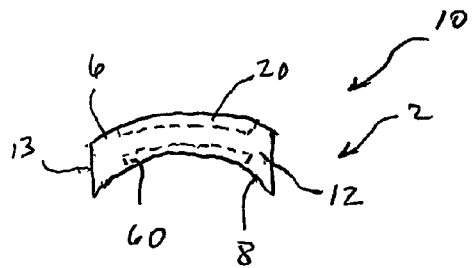

The present invention hand held system may be curved so as to fit the shape of the target or a partial area of the target, such as a patient or inanimate object. For example, FIGS. 8A-8B, show a schematic longitudinal perspective view and lateral side view, respectively, of the hand held ultrasonic system 10 wherein the curve of the display 20, housing 2, and/or transducer array 60 is in the longitudinal direction (any select one of these components or combination thereof, as well as other system components may be curved). Some components Whereas, FIGS. 9A-9B, show a schematic longitudinal perspective view and lateral side view, respectively, of the hand held ultrasonic system 10 wherein the curve of the display 20, housing 2, and/or transducer array 60 is in the lateral direction (any select one of these components or combination thereof, as well as other system components may be curved). One should appreciate that the longitudinal and lateral curves may be combined to form various shapes and contours.

In an embodiment, the present invention ultrasound system and method proves particularly valuable for continuous monitoring of obstructive sleep apnea. Sleep apnea (obstruction of the air passage in the throat) is highly prevalent, affecting more than eighteen million Americans. Amongst the variants of sleep apnea, obstructive sleep apnea is by far the most common. It is difficult and expensive to diagnose and represents a significant risk to the patient. Typical diagnostic methods require an overnight hospital stay in an instrumented laboratory. Many at risk patients refuse this inconvenient testing regime and thus go undiagnosed. The present invention low cost sonic window can be coupled with relatively simple image processing to directly diagnose obstructive sleep apnea in a minimally obtrusive manner. Such an approach could be used in both initial diagnosis and as a warning device in chronic cases.

In an embodiment, the present invention ultrasound system and method proves particularly valuable as an adjunct to palpation. Manual palpation is an exceedingly common diagnostic procedure. Clinicians use their sense of touch to feel for subcutaneous lumps or even to estimate the size of lymph nodes or other masses. While palpation undoubtedly yields valuable qualitative information, numerous studies have shown it to have extremely poor sensitivity and that quantitative size estimates are completely unreliable. The present invention sonic window would offer a new method and system of observing subcutaneous tissues. It can be appreciated that various applications can be utilized, including providing more reliable and quantitative information than simple manual palpation.

In an embodiment, the present invention ultrasound system and method proves particularly valuable for non-destructive evaluation. In a broad variety of industrial applications ultrasound is used to search for internal defects in metallic or ceramic parts. Current systems are cost effective, but are unwieldy and acquire limited data, making it difficult to ensure that a thorough search has been performed. The present invention sonic window allows for more rapid and thorough examination than current techniques, and at a competitive cost.

EXAMPLES

The following example is intended for illustrative purposes only and is not intended to be limiting in any manner.

Example No. 1

Referring to FIG. 7, a schematic block diagram of an embodiment of the invention is shown, whereby a two-dimensional piezoelectric transducer array 60 is utilized. The transducer array 60 consists of a 32×32 element array of 500×500 un elements 62. These elements can be constructed by using a commercially available wafer dicing saw to cut a Lead Zirconate Titanate (PZT) ceramic that had been mounted to a printed circuit board. While the printed circuit board does not provide optimal acoustic properties, it can be easily fabricated at a low cost. Selection of non-standard materials as the substrate for the printed circuit board (such as a thermoplastic) will enable some control over the acoustic response of the transducer. The printed circuit board provides the connection to one side of the elements 62. The other side of the elements is tied to a common ground plane by adhering a foil layer to the surface using an electrically conductive epoxy.

A transmit-receive switch 70 would be connected directly to the transducer elements. This switch acts 70 to ensure that either transmit or receive circuitry 75 is connected to the transducer elements 62, but never both simultaneously. This is essential since the high transmit voltages (on the order of about 50-200 Volts) would damage the sensitive amplifiers used in echo reception. Furthermore, the preferred embodiment utilizes a CMOS integrated circuit. Such CMOS processes are relatively easily damaged by the application of high voltage.

In one embodiment of this invention the transmit-receive switch and transmit circuitry are integrated in such a manner as to reduce cost and complexity.

A preferred embodiment maintains low cost and system performance by integrating the preamplifiers 71, amplifiers 72, A/D converters 73, buffer RAM 74, and beamformer 40 into a single CMOS integrated circuit. A single integrated circuit could include a large number of channels, that is, all the circuitry required for reception and focusing of some large number of elements. A preferred embodiment would include all these circuit components for all 1024 elements on a single integrated circuit.

The preamplifiers 71 provide electrical impedance matching between the transducer elements 62 and the receiving electronics. They also provide some small amount of fixed gain. The amplifier stage provides a more significant level of gain that is adjustable to account for signal losses due to frequency dependent attenuation. The analog to digital converters (A/D converters) 73 digitize the received echoes at 8 bits and a nominal sampling frequency of 40 MHz. Sampled data is then stored temporarily in the buffer RAM 74. Sampled data is read from this buffer RAM by the beamformer 40. The beamformer delays the echo signals differentially to focus the signals on the location of interest. These delays may have a smaller interval than the sampling interval by employing digital interpolation filters. Once the echo signals have been appropriately delayed they may be summed together to yield the focused signal for a single line through the tissue. One skilled in the art would appreciate that the aforementioned focal delays might be updated at rapid intervals to perform what is commonly known as "dynamic focusing."

Focused echo data coming out of the beamformer would be processed further by a general purpose digital signal processor (DSP) 41 such as the Texas Instruments TMS320C55 DSP processor. This DSP 41 processes the focused line data by performing envelope detection and mapping the envelope detected data to the appropriate location in the image display. Finally, the image data would be displayed using an LCD screen 20 such as those employed in handheld televisions, personal digital assistants, or laptop computers.

Transmit timing, focal parameters, image depth, image gain, and other parameters could be determined by a system control unit 80. This control unit 80 could consist of a second DSP chip like the one described above. This chip would read user controls and update system settings to implement user adjustments. This control unit might also employ an interface to an external storage device and an interface to an external printer.

The following U.S. patents are hereby incorporated by reference herein in their entirety:

U.S. Pat. No. 4,240,295 to Uranishi, entitled "Ultrasonic Diagnosing Apparatus;"

U.S. Pat. No. 5,065,740 to Itoh, entitled "Ultrasonic Medical Treatment Apparatus;"

U.S. Pat. No. 5,097,709 to Masuzawa et al., entitled "Ultrasonic Imaging System;"

U.S. Pat. No. 5,722,412 to Pflugrath et al., entitled "Hand Held Ultrasonic Diagnostic Instrument;"

U.S. Pat. No. 5,879,303 to Averkiou et al., entitled "Ultrasonic Diagnostic Imaging of Response Frequency Differing from Transmit Frequency;"

U.S. Pat. No. 5,833,613 to Averkiou et al., entitled "Ultrasonic Diagnostic Imaging with Contrast Agents;"

U.S. Pat. No. 5,893,363 to Little et al., entitled "Ultrasonic Array Transducer Transceiver for a Hand Held Ultrasonic Diagnostic Instrument;"

U.S. Pat. No. 6,106,472 to Chiang, et al., entitled "Portable Ultrasound Imaging System;"

U.S. Pat. No. 6,241,673 to Williams, entitled "Diagnostic Medical Ultrasound System with Wireless Communication Device;"

U.S. Pat. No. 6,283,919 to Roundhill et al., entitled "Ultrasonic Diagnostic Imaging with Blended Tissue Harmonic Signals;"

U.S. Pat. No. 6,383,139 to Hwang et al., entitled "Ultrasonic Signal Processor for Power Doppler Imaging in a Hand Held Ultrasonic Diagnostic Instrument;"

U.S. Pat. No. 6,436,040 to Collamore et al., entitled "Intuitive User Interface and Control Circuitry Including Linear Distance Measurement and User Localization in a Portable Ultrasound Diagnostic Device;"

U.S. Pat. No. 6,440,072 to Schuman et al., entitled "Medical Diagnostic Ultrasound Imaging System and Method for Transferring Ultrasound Examination Data to a Portable Computing Device;"

U.S. Pat. No. 6,488,625 to Randall et al., entitled "Medical Diagnostic Ultrasound System and Method;" and U.S. Pat. No. 6,497,661 to Brock-Fisher, entitled "Portable Ultrasound Diagnostic Device with Automatic Data Transmission."

In conclusion, in view of the foregoing, an advantage of the present invention ultrasonic imaging system and method provides is ease of use, whereby acquiring and displaying data in the intuitive C-Mode format little or no training will be necessary for clinicians to make use of the device.

Another advantage of the present invention ultrasonic imaging system and method is low cost, whereby large scale integration of the beamformer will enable the system to be produced at a very low cost. This will open numerous applications for which ultrasound was previously cost prohibitive.

Still yet, another advantage of the present invention ultrasonic imaging system and method is portability, whereby the small size of the system will make it easy to carry in a pocket or on a belt attachment. This will make the system or device as available as a stethoscope and will thus open new applications.

Further, another advantage of the present invention ultrasonic imaging system and method is that there are no low cost, portable systems that produce C-Mode displays.

Moreover, another advantage of the present invention is that it can be battery operated without a power cord or the like.

Finally, another advantage of the present invention is that entanglement of transducer cable is avoided.

The present invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced herein.

We claim:

1. An ultrasonic imaging system capable of producing images of a target, said system comprising:
   a housing;
   a two-dimensional transducer array disposed on said housing;
   a display unit disposed on said housing, the display unit defining a planar region, wherein said transducer array and said display unit are integrated with the housing, wherein said display unit lies in a plane that is substantially parallel to said two-dimensional transducer array;
   a beamformer disposed within said housing, said beamformer in communication with said two-dimensional transducer array, and generating focused echo data; and
   an image processor disposed within said housing, said image processor receiving said focused echo data and generating an image corresponding to an image plane located below the plane of the display, wherein said image represents a portion of said image plane that is in substantial alignment with said planar region of said display unit.

2. The system of claim 1, further comprising a control to select the depth of the image plane.

3. The system of claim 2, wherein the control is a thumbwheel.

4. The system of claim 1, wherein said image plane displayed on the display unit is scaled in a manner so that dimensions of the image correspond with dimensions of the target.

5. The system of claim 1, wherein the image is formed from a 3D data set by compounding a plurality of adjacent image planes, each image plane located at a different depth.

6. The system of claim 1, wherein said system weighs less than about 5 pounds.

7. The system of claim 1, wherein said system weighs less than about 2 pounds.

8. The system of claim 1, wherein said housing has a volume of less than about 4 cubic inches.

9. The system of claim 1, wherein said housing has a volume of less than about 48 cubic inches.

10. The system of claim 1, wherein said display unit is adjustably mounted to said housing; and
    wherein the image plane is at an angle with respect to the two-dimensional transducer array.

11. The system of claim 10, wherein an adjustment of an angle of said display unit controls the image plane angle.

12. The system of claim 11, wherein the angle of said display unit is substantially equal to the image plane angle.

13. The system of claim 1, wherein said image displayed on said display unit is scaled in a manner whereby dimensions of said image corresponds with dimensions of the target.

14. The system of claim 1, wherein said image displayed on said display unit is scaled in a manner that magnifies the dimensions of the target.

15. The system of claim 14, wherein said system further comprises a user control unit, wherein said image displayed on said display unit is scaled in response to said user control unit.

16. The system of claim 1, wherein said image displayed on said display unit is a C-Mode image of tissue, whereby said displayed image is obtained in a plane substantially parallel or exactly parallel to the face of the transducer.

17. The system of claim 1, wherein said image displayed on said display unit is an animation comprising a plurality of images from image planes having different depths within a target.

18. The system of claim 1, wherein said image is formed by averaging at least two envelope detected images from multiple parallel planes, whereby appearance of speckle in the displayed image is reduced.

19. The system of claim 1, wherein said image represents estimated blood flow velocities encoded in color.

20. The system of claim 1, wherein said image depicts Power Doppler information.

21. The system of claim 1, wherein said image depicts tissue harmonic information.

22. The system of claim 1, wherein said image is formed by transmit-receiving compounding.

23. The system of claim 1, wherein said image is formed by receive only spatial compounding.

24. The system of claim 1, wherein said image is formed by frequency compounding.

25. The system of claim 1, wherein said image depicts speckle pattern decorrelation over time as a means to identify tissue or blood motion.

26. The system of claim 1, wherein said two-dimensional transducer array transmits ultrasonic energy into a target, wherein the ultrasonic energy transmitted uses one or more focused transmit beams.

27. The system of claim 1, wherein said two-dimensional transducer array transmits ultrasonic energy into a target, wherein the ultrasonic energy transmitted uses an unfocused transmit beam.

28. The system of claim 1, wherein said two-dimensional transducer array transmits ultrasonic energy into the target, and said two-dimensional transducer array being responsive for receiving ultrasonic echo signals from the target, said two-dimensional transducer array using a coded excitation scheme to increase the effective signal to noise ratio of received echo signals.

29. The system of claim 1, further comprising:
at least one passage in communication with said system, said system being adapted to correlate location of said passage with the target.

30. The system of claim 29, wherein a needle or tool inserted into said passage displayed on said display unit.

31. The system of claim 29, wherein at least one of said at least one passage is disposed on at least one of said transducer array and/or housing.

32. The system of claim 1, further comprising:
a marker unit, said marker unit adapted for placing one or more marks on a target.

33. The system of claim 1, wherein said two-dimensional transducer array is comprised at least in part of a piezoelectric material.

34. The system of claim 1, further comprising:
at least one removable cover, at least one said cover at least partially covering said housing.

35. The system of claim 34, further comprising:
at least one adhesive device, at least one said adhesive device at least partially disposed on said cover.

36. The system of claim 34, further comprising:
at least one intake disposed on said cover, said intake allowing access through said cover.

37. The system of claim 1, further comprising:
at least one adhesive device, at least one said adhesive device at least partially covering said housing.

38. The system of claim 1, further comprising:
at least one retaining device, at least one said retaining device at least partially disposed on said housing.

39. The system of claim 1, wherein at least one of said housing, display, and two-dimensional transducer array is curved.

40. A method of imaging a target to produce ultrasonic images, comprising the steps of
providing a housing;
providing a two-dimensional transducer array disposed on said housing,
transmitting ultrasonic energy into the target and receiving ultrasonic echo signals from the target with said two-dimensional transducer;
beamforming said received echo signals to provide beamformed data;
processing said beamformed data to form a C-mode image; and
providing a display unit disposed on said housing,
displaying said C-mode image on said display unit, wherein said display unit is adjustable at an angle relative to said housing, and adjusting an image plane of said displayed image based on said angle of said display unit.

41. The method of claim 40, wherein said beamformer is disposed on said housing.

42. The system of claim 29, wherein the location correlation function is achieved by at least one intersection point indicator displayed on said display unit, at least one said intersection point indicator corresponds with at least one desired intersection point on the target and/or at least one image plane of the target.

43. A method of imaging a target to produce ultrasonic images comprising:
obtaining ultrasonic echo signals from a target using a two-dimensional transducer array;
generating a two-dimensional image via an image processor using the ultrasonic echo signals for presentation on a display unit, wherein the display unit is in substantial alignment with the two-dimensional transducer, and wherein the display unit, the image processor and the two-dimensional transducer are collocated within a housing; and
wherein the two-dimensional image corresponds to an image plane that is located underneath the two-dimensional transducer array and is in substantial alignment with the two-dimensional transducer array and the display unit.

44. The method of claim 43 wherein the image plane is substantially parallel to the two-dimensional transducer array.

45. The method of claim 43 wherein the image plane is located at a depth beneath the two-dimensional transducer array, where in the depth is selectable.

46. The method of claim 43 wherein the image plane is sloped with respect to the two-dimensional transducer array.

47. The method of claim 46 wherein the slope is selectable.

48. The method of claim 43 wherein the two-dimensional image is formed by averaging at least two envelope detected images from image planes at different depths, whereby appearance of speckle in the displayed image is reduced.

49. The method of claim 43 wherein the two-dimensional image comprises an animation of a plurality of images from image planes having different depths within a target.

* * * * *